Figure 1:
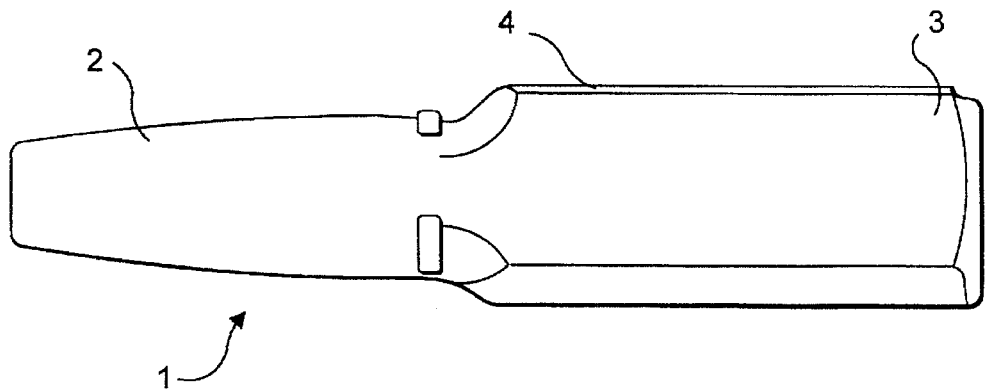

United States Patent [19]

Mortensen

[11] Patent Number: 5,641,184

[45] Date of Patent: Jun. 24, 1997

[54] TUBE, ESPECIALLY FOR MEDICAL USE, METHOD OF PRODUCING SAID TUBE, AND TOOL FOR USE IN THE IMPLEMENTATION OF THE METHOD

[75] Inventor: Erik Meier Mortensen, Præstø, Denmark

[73] Assignee: Maersk Medical A/S, Lynge, Denmark

[21] Appl. No.: 356,363

[22] PCT Filed: Jul. 2, 1993

[86] PCT No.: PCT/DK93/00223

§ 371 Date: Dec. 22, 1994

§ 102(e) Date: Dec. 22, 1994

[87] PCT Pub. No.: WO94/01171

PCT Pub. Date: Jan. 20, 1994

[30] Foreign Application Priority Data

Jul. 6, 1992 [DK] Denmark .................. 0887/92

[51] Int. Cl.[6] ........................................ F16L 35/00
[52] U.S. Cl. .................. 285/93; 285/423; 264/35; 264/271.1; 425/453

[58] Field of Search ................ 285/93, 284, 423; 425/453, 467, 348 S, 412; 264/35, 271.1

[56] References Cited

U.S. PATENT DOCUMENTS

| 3,898,988 | 8/1975 | Morgan | 285/93 X |
| 3,990,445 | 11/1976 | Lundquist | 285/93 X |
| 4,214,779 | 7/1980 | Losell | 285/93 |

FOREIGN PATENT DOCUMENTS 675902  11/1990  Switzerland ............ 285/239

*Primary Examiner*—Dave W. Arola
*Attorney, Agent, or Firm*—McAulay Fisher Nissen Goldberg & Kiel

[57] ABSTRACT

A tube made of plastic with a body in the wall of the tube which body can be pierced by a hypodermic needle. The body has sealing elements extending therefrom. The tube is molded around the body and sealing elements. A tool is provide which includes an upper and lower portions with the body being initially molded in the upper portion and then the portions are rotated 180 degrees and the tube is then molded around the body.

10 Claims, 6 Drawing Sheets

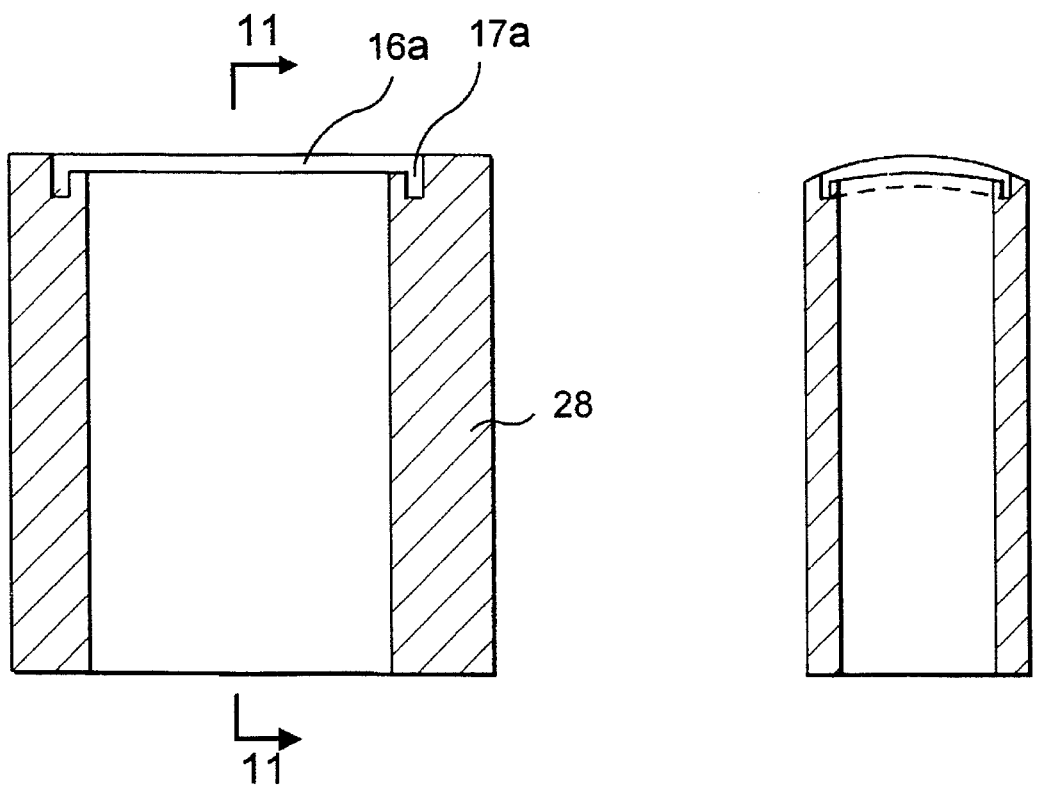
FIG. 9
FIG. 11
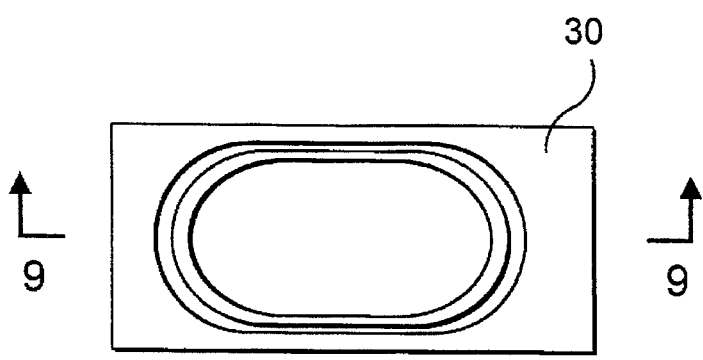
FIG. 10

TUBE, ESPECIALLY FOR MEDICAL USE, METHOD OF PRODUCING SAID TUBE, AND TOOL FOR USE IN THE IMPLEMENTATION OF THE METHOD

The invention relates to a tube of plastic and with an insertion end, an intermediate portion, and a receiving end, which tube is adapted to connect a hose to a spigot end, especially for medical use, and where the intermediate portion in a first half part of the tube comprises an elastic deformable body arranged in a hollow in the tube wall, which body is to be pierced by a hypodermic needle point, and which body along its circumference has sealing elements concurring with the tube.

Furthermore, the invention relates to a method of producing the tube as well as a tool for implementation of the method of producing several of the mentioned tubes.

For medical use it is common practise that several devices are to be connected with each other in order to produce a flow passage for a fluid, such as a liquid or a gas. The devices are thus provided with coupling elements which are firmly mounted on the individual device.

The coupling elements often comprise an insertion portion in the form of a tube on the one device and a receiving portion on the second device.

The insertion portion is configured as a short tube having a tapered end, and the receiving portion is configured as a muff the bore of which converges conically inwards towards the device. The size of the mentioned tapered parts is adapted to the material of the coupling elements in such a manner that the parts can remain in their coupled position by means of friction or gluing.

In order to avoid an exact alignment of the coupling elements on two devices that are to be coupled together generally hoses are used to connect the coupling elements.

During application of the devices it is often necessary to take a sample of a fluid being transported from one device to another or to add a substance or liquid to the mentioned fluid.

Thus it must be ensured that no fluid leaks out or that the fluid is not contaminated during such tests or injections. This object is achieved by sticking a hypodermic needle point into the flow passage.

The applied hoses are, however, of such a kind or such material that piercing by a hypodermic needle is not advisable.

Consequently, a tube of plastic has been produced, which tube has an elastic deformable body arranged in the tube wall, which body is arranged to be pierced at least once by a hypodermic needle point, partly as the body closes tightly round the needle during insertion and contracts tightly when the needle is withdrawn, so that no fluid may leak out from the flow passage or any contamination may enter the flow passage during or after the sampling or testing.

However, there is a drawback to the known tube in that it does not close sufficiently tight to the hollow in the tube wall, and thus fluid and/or contamination may pass through the joint between the body and the hollow in the tube wall. It may occur that the body during piercing by the needle point is pushed into the through-going bore of the tube or that the body is pulled out of the tube hollow during withdrawal of the hypodermic needle.

This is due to the fact that the body in the known tube is merely stuck into the hollow from the outside of the tube, which hollow wall extends rectilinearly against the longitudinal bore in the tube, whereupon the body is secured in the hollow solely by the friction between the two parts, as the dimension of the body is somewhat larger than that of the hollow, so that the body exercises a force against the wall of the hollow due to the deformation.

The object of the present invention is to provide a configuration of the known tube which can produce sufficient sealing between the body and the hollow of the tube wall, so that the mentioned drawback is avoided, as the object of the invention is also to provide a method for a secure and safe placing of the body in the hollow of the tube wall as well as to provide a tool for use in the implementation of the method mentioned.

This object is achieved with a tube of the type referred to above, which tube according to the invention is characteristic in that the sealing elements comprise at least a first wall projecting from the circumference of the body, which wall extends parallel with and coaxially round the axis of the tube and a flange projecting from the edge of the first wall, which flange extends a short distance in the direction of the inner wall of the intermediate portion of the tube, which first wall and flange are in form-close connection with corresponding recesses in the wall of the hollow.

The sealing elements of the body thus configured and thus concurring with the wall in the hollow of the tube produce a specially safe sealing between the body and the hollow in the tube, as the sealing is improved in that the wall of the hollow, as with the known tube, does not extend rectilinearly but is interrupted by the sealing elements, and at the same time it is efficiently prevented that the body is displaced in the tube hollow for the body.

The first wall and flange constitute together with the corresponding recesses a labyrinth sealing which offers extraordinary strong sealing against leaking out of fluid from the flow passage or against leaking in of contamination into the flow passage.

If the fluid in the flow passage is under pressure it offers the advantage that the sealing elements comprise a second wall which extends parallel to the first wall and is configured to abut against the inner wall of the intermediate portion of the tube.

The fluid pressure pushes the second wall against the inner wall of the tube thus improving the sealing.

It will be understood that it is extraordinary difficult to arrange the body in the hollow of the tube solely by pressing the body into the hollow, as the projecting sealing elements will counteract this, and it would furthermore be impossible simply by pressing in to produce a form-close connection between the sealing elements and the recesses in the hollow when the sealing elements are configured as defined.

Therefore a method of producing the defined tube is provided, which method according to the invention is characteristic in that the body is moulded in a first mould part, that the moulded body remaining in the first mould part is displaced to a second mould part in such a manner that the body in the second mould part with a surface abuts against a core and with an opposite surface abuts against the inner wall of a section of the first mould part, which section can mould the intermediate portion of the tube, whereupon the remaining part of the tube is moulded in the cavity space being formed by the first mould part together with the second mould part, the core and the body in form-close engagement with the body and its sealing elements.

The mentioned displacement from the first to the second mould part can thus be carried out without contaminating the body, which may result in insufficient sealing between the body and the wall of the hollow.

The tool according to the invention is characteristic in that the tool comprises an upper and a lower portion, that the upper portion has an even number of first mould parts each configured for moulding the first mould part of a tube, which first mould parts extend mutually parallel with one half part in a primary portion and a second half part in a secondary portion, which primary and secondary portion extend on each side of an axis which is common for the upper and lower portion, that elements for moulding a body are provided in each of the mould parts in the primary portion of the upper portion, that the lower portion on a level with the mentioned primary portion of the upper portion has elements which together with the elements in the mould parts are used for moulding a body and opposite the mentioned secondary portion has a number of other mould parts corresponding to half of the number of the first mould parts, which other mould parts together with cores constitute a cavity corresponding to the shape of the tubes, which upper and lower portions of the tool may be turned relatively 180° on the common axis in such a manner that the first mould parts in the primary and secondary portion, respectively, in turn can be made to concur with the other mould parts in the lower portion, and that the tool has elements to displace bodies that are moulded in the first mould parts to the other mould parts in the lower portion in such a manner that the bodies are inserted and secured in the mentioned cavities abutting partly against the cores and partly against the inner wall of a section in the other mould parts, which sections can mould the intermediate portion of the tubes.

The dependent claims define advantageous configurations of the features in the independent claims.

Figure 2:
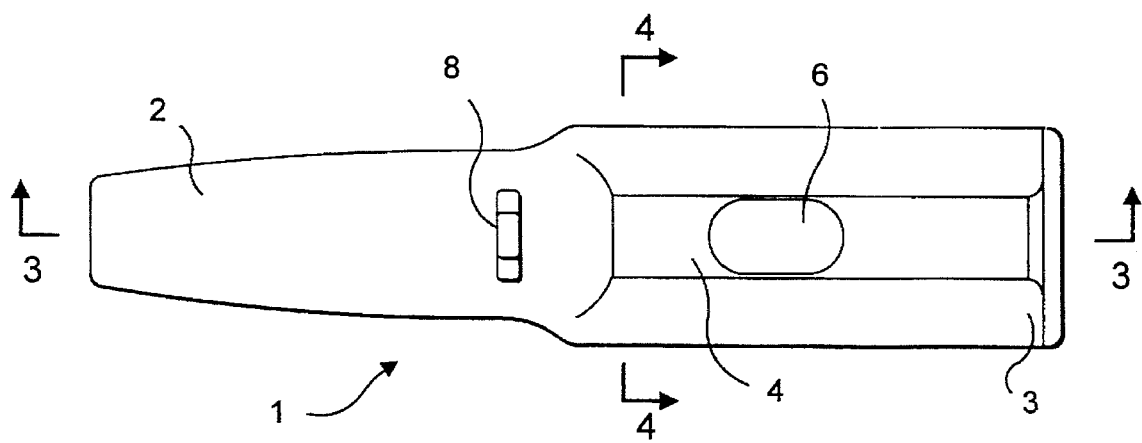
Figure 3:
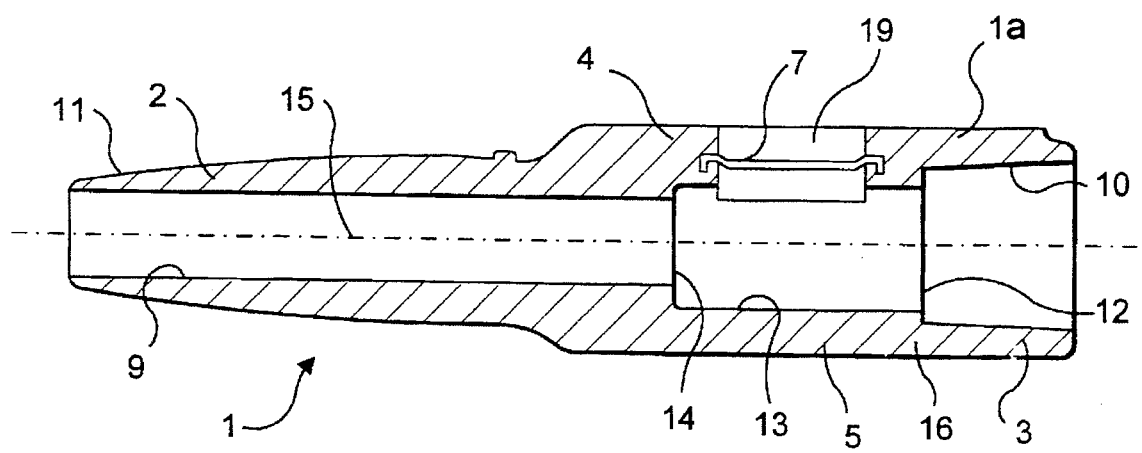
Figure 4:
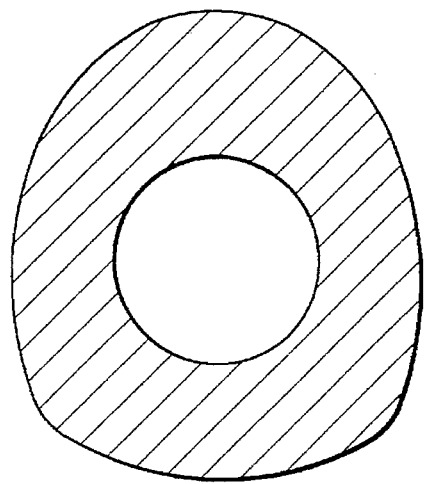
Figure 5:
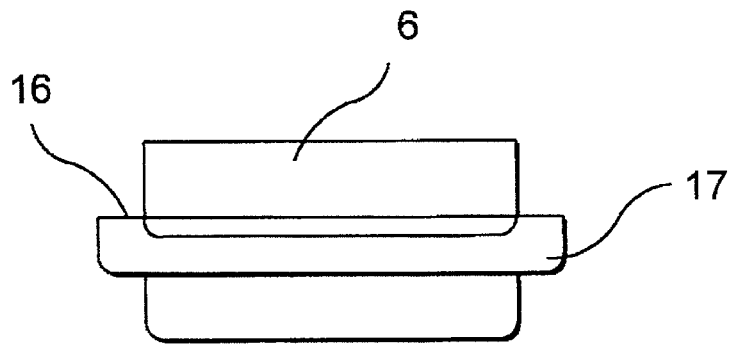
Figure 6:
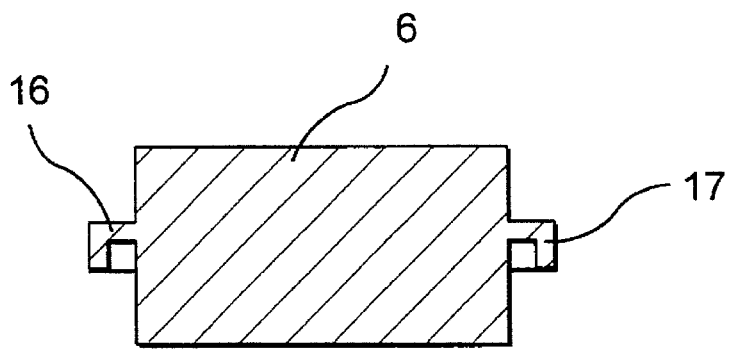
Figure 7:
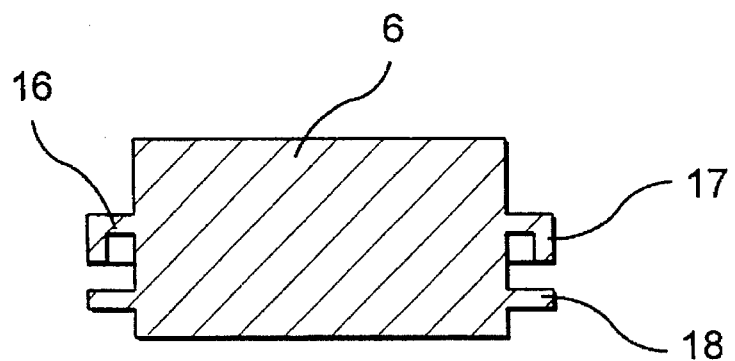
Figure 8A:
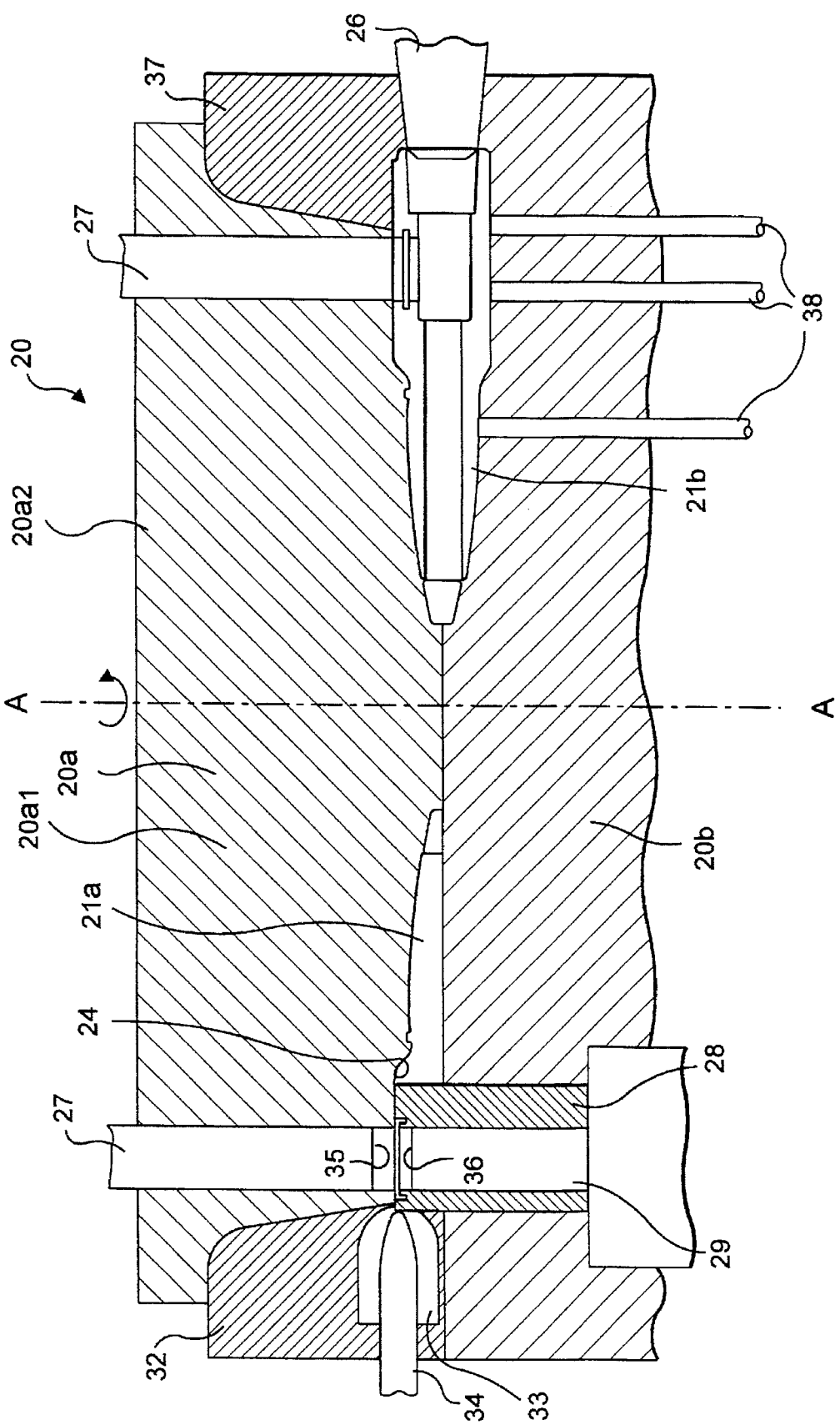
Figure 8B:
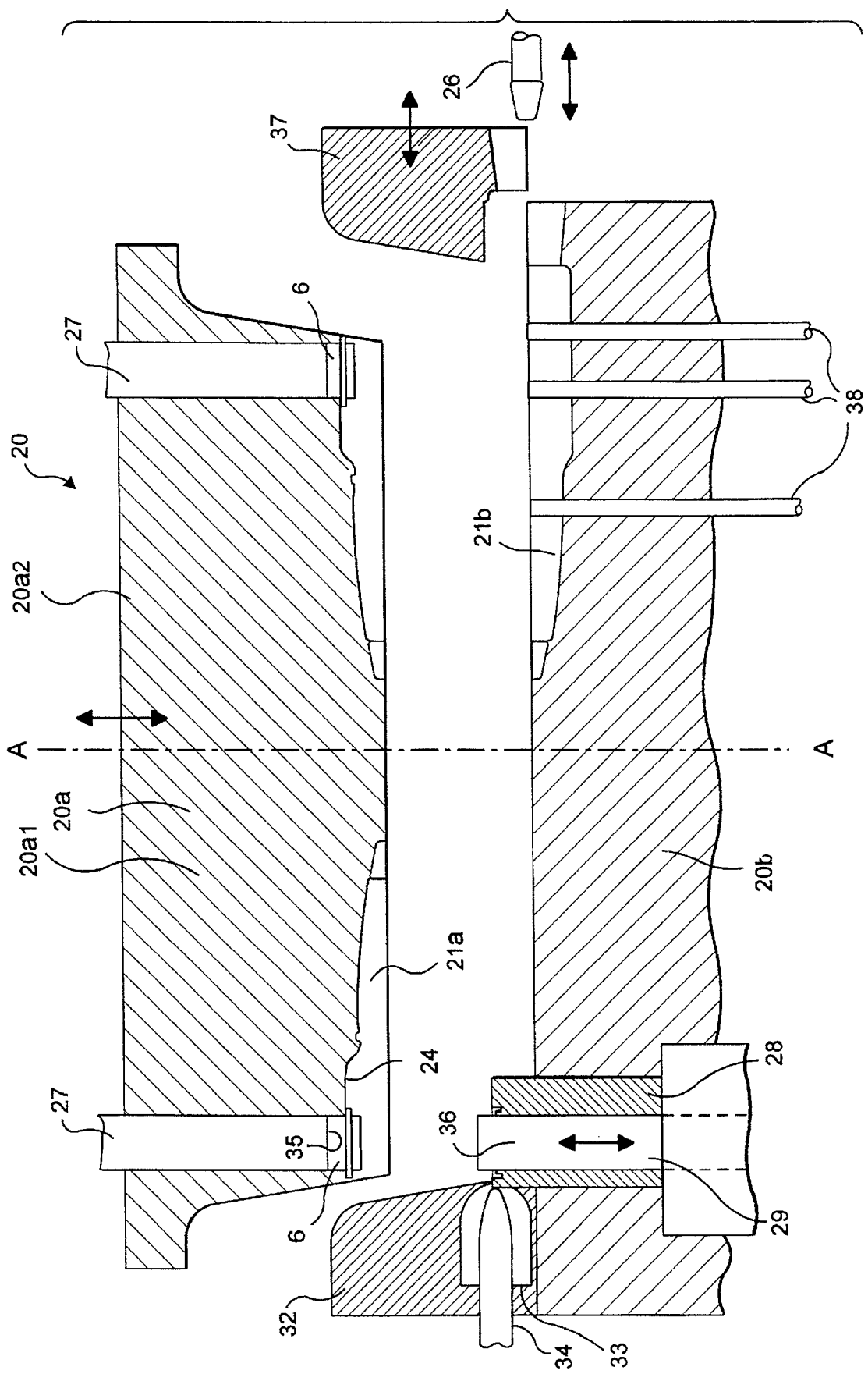

The tube according to the invention, the method of producing the tube as well as the tool for use in implementation of the method will be explained in detail with reference to the drawing, wherein FIG. 1 is a side view of the tube according to the invention, FIG. 2 is a top view of the tube according to FIG. 1, FIG. 3 is a longitudinal section of the tube in FIG. 2 indicated by the line III—III, FIG. 4 is a section of the tube in FIG. 2 indicated by the line IV—IV, FIG. 5 is a side view of the deformable body in a first configuration, dismounted from the tube, FIG. 6 is a longitudinal section in the first configuration in FIG. 5, FIG. 7 is a longitudinal section in a second configuration of a deformable body dismounted from the tube, FIG. 8a–8b is a section of a tool for use in the implementation of several tubes according to the invention in the closed and opened position, respectively, of the tool, which section extends along an axis of the tool, FIG. 9 is a section of a negative mould indicated by the line IX—IX in FIG. 10, FIG. 10 is a top view of the negative mould, and FIG. 11 is a section in the negative mould indicated by the line XI—XI in FIG. 9.

In the drawing 1 refers to a tube according to the invention, which tube is preferably for medical use and is generally made of plastic or a corresponding material with physical qualities which will satisfy the requirements regarding use of the tube.

The first end and the opposite second end of the tube 1 are referred to by 2 and 3, respectively. The first end is preferably configured as an insertion end, and the opposite second end is configured as a receiving end. Between the insertion end 2 and the receiving end 3 is an intermediate portion 4. The tube 1 has a through-going bore 9, 13, 10. The outer free end 11 of the insertion end 2 is tapered and the outer section 10 of the bore at the receiving end 3 has a corresponding tapering, so that another tube 1 can be inserted and secured in the receiving end, for example by friction or gluing.

At the link between the outside of the insertion end 2 and the intermediate portion 4 are three radially projecting knobs 8 that are evenly spread on the surface of the insertion end 2. Each knob 8 extends over less than 60° of the mentioned surface. The knobs 8 offer the possibility of using means which can ensure securing of the tube 1 to a device where a connection must be fully guaranteed.

At the inner end of the tapered section 10 in the receiving end 3 is an offset 12 which forms the link to the cylindrical bore 13 extending in the direction of the insertion end 2 and is ended by another offset 14, from which the cylindrical bore 9 continues to the free end of the insertion end 2.

The tapered section 10, the cylindrical bores 9, 13, and the free end 11 of the insertion end 2 extend coaxially on the axis 15 of the tube 1.

A plane through the axis 15 of the tube 1 divides the tube 1 into a first half part 1a and a second half part 1b.

In the wall 5 of the intermediate portion 4 is a hollow 19 in the first half part 1a, in which hollow 19 is arranged an elastic deformable body 6 which may be penetrated by a hypodermic needle, so that a substance can be injected into or a sample can be made from a fluid by means of a hypodermic needle, which fluid flows through the tube 1 in the cylindrical bores 9, 13.

Upon the injection or the sampling the elastic deformable body 6 will seal itself after withdrawal of the hypodermic needle.

The body 6 and the hollow 19 have concurring sealing elements 7 which ensure that a fluid being transported through the cylindrical bores 9, 13 in the tube 1 can not leak into the intermediate space between the body 6 and the wall of the hollow 19.

The mentioned concurring sealing elements 7 are provided in order to produce compactness between the circumference of the body 6 and the wall in the hollow 19.

These sealing elements 7 are in the form of a labyrinth sealing which in a first configuration consists of a roughly perpendicularly projecting wall 16 which extends parallel with and coaxially round the axis 15 of the tube 1 when the body 6 is arranged in the hollow 19. At the outer edge of the wall 16 is a flange 17 extending a short distance in the direction of the axis 15 which can be seen most clearly in FIG. 6.

The projecting wall 16 and the flange 17 are form-closely received by a recess arranged in the wall of the hollow 19.

In cases where particular requirements in regard of a secure sealing is called for the body 6, in another embodiment, can be provided with a further projecting wall 18, which wall extends parallel with the wall 16 and along the edge of the body 6, which edge faces the axis 15 of the tube 1 when the body 6 is arranged in the tube 1.

The further projecting wall 18 may be form-closely received by a recess at the link between the hollow 19 and the cylindrical bore 13 in the tube 1, however, in a simpler embodiment the projecting wall 18 may merely abut against the wall of the cylindrical bore 13.

It will be understood that it is extraordinarily difficult to arrange the body 6 with the projecting wall 16 and the flange 17 in the hollow 19 of the tube 1 when the hollow has a recess for form-close receiving of the wall 16 and the flange 17.

Therefore a method of producing the tube 1 has been invented so that subsequent placing of the body 6 in the tube 1 can be avoided.

By the method according to the invention the body 6 is produced in a first mould part 21a whereupon the completely shaped body 6 remaining in the first mould part 21a is displaced to a second mould part 21b comprising a core 26 and dismantable moulding parts which together with the first mould part 21a form a cavity corresponding to the tube 1, as the shaped body 6 constitutes one of the mentioned moulding parts. The body 6 is thus inserted between a moulding part, which can form the outside of the tube wall 5, and the mentioned core 26.

During the transfer to the second mould part 21b the body 6 is secured in the first mould part 21a so that manual handling of the body 6 is avoided. By this mechanical transfer any contamination of the body 6 is avoided which is very important, as any contamination would result in insufficient sealing between the body 6 and the tube 1.

For use in implementation of the method a tool 20 is provided according to the invention, in which tool the tube 1 with a body 6 ready mounted in the hollow 19 can be produced.

This tool is to be placed in a machine for the moulding of plastic, which machine consists of two main elements hereinafter referred to as the upper portion 20a and the lower portion 20b, however, it must be taken to mean that a necessary orientation of the two portions in relation to each other is not indicated by the terms upper and lower portions and that the two portions can thus be arranged next to each other during use of the tool.

The two portions 20a and 20b can be moved towards and away from each other along a common axis A—A round which they also can be turned relatively stepwise 180°. A plane through the axis A—A divides the upper portion 20a into a primary portion 20a1 and a secondary portion 20a2.

In the upper portion 20a are provided an even number of recesses or mould parts 21a in the surface facing the surface of the lower portion 20b, which recesses or mould parts 21a extend mutually parallel and are arranged with one half part on each side of the axis A—A, i.e. a first half part in the primary portion 20a1 and the second half part in the secondary portion 20a2. Each mould part 21a comprises a cavity corresponding to the first half part 1a of a tube 1 from its insertion end 2 and to an imaginary cross-section in the tube, which cross-section touches the part of the flange 17 of the body 6 which is closest to the receiving end 3 of the tube.

In each of these mould parts 21a is a positive mould 27 which can be displaced parallel along the axis A—A between a protruding position where the surface 35, ending at the mould part 21a, just flushes with the inner wall 24 of the section in the mould part 21a which can shape the intermediate portion 4 of a tube 1 and a withdrawn position in the upper portion 20a where the mentioned surface 35 is positioned at a distance from the mentioned inner wall 24 which equals the distance from the projecting wall 16 of a body 6 and to the outside surface of the intermediate portion 4 of the tube 1.

Furthermore, in the lower portion 20b is provided a projecting negative mould 28 on the surface for each mould part 21a facing the primary portion 20a1, which projecting negative mould has a surface 30 which in the closed position of the tool can abut against and concur closely with the inner wall 24 in the mould part 21a. In the surface 30 is a recess 16a, 17a which is complementary in relation to the parts of the projecting wall 16 and the flange 17 which parts face the axis 15 of the tube 1. The negative mould 28 is fixedly mounted in the lower portion 20b.

The negative mould 28 encloses an ejector 29 which has a surface 36 facing the upper portion 20a, the shape of the surface being complementary to the shape of the cylindrical bore 13 in a tube 1 or the shape of the surface of a body 6 which in a completely shaped tube 1 faces the axis 15 of the tube and which surface is to flush with the wall of the bore 13. The ejector 29 is displacably mounted in the lower portion 20b in such a manner that the mentioned surface 36 is positioned a distance from the surface 30 of the negative mould 28 which surface equals the distance from the projecting wall 16 and to the inner wall of the cylindrical bore 13 in a tube 1 when the negative mould 28 in the closed position of the tool abuts against the inner wall 24 of the mould part 21a. The ejector 29 is affected by a spring which is not shown in the drawing, so that the ejector 29, when the tool is opened, is displaced parallel with the axis A—A and partly towards the upper portion 20a, so that the surface 36 of the ejector 29 projects from the surface 30 of the negative mould 28. The movement of the ejector 29 in relation to the negative mould 28 is limited to a length which is only somewhat larger than the dimension of a body 6 seen in the direction of the axis A—A.

In connection with the mould parts 21a a casting box 32 is arranged on the side of the lower portion 20b which casting box in the drawing has channels which are not shown for feeding of the elastic deformable material for producing a body 6. The material is fed through a chamber 33 which ends directly in or at the mould 21a in order to avoid spilled material left in the channels, as this spillage would constitute a considerable loss of valuable material and would also involve considerable work performed in order to remove the spillage. The material is kept at a temperature suitable for moulding by means of a commonly known heating stick 34.

From the above it will be understood that the positive mould 27 in its withdrawn position together with the ejector 29 and the negative mould 28 constitutes a cavity in which a body 6 can be moulded when the upper portion 20a abuts against the lower portion 20b and moulding material is fed from the casting box 32.

Apart from the negative moulds 28 and the ejectors 29 the lower portion 20b has a number of other mould parts 21b corresponding to half of the number of the first mould parts 21a, which other mould parts 21b are arranged on the opposite side of the axis A—A i relation to the negative moulds 28 and the ejectors 29. These other mould parts 21b are in other words arranged opposite the mould parts 21a in the secondary portion 20a2 of the upper portion 20 of the tool. The other mould parts 21b have a shape corresponding to the other half part 1b of a tube 1 and constitute together with a half part of the first mould parts 21a a cavity suitable for moulding the outer surface of a tube 1. In order to produce the bore 9, 13, 10 in the tubes cores 26 are provided which can be inserted from the side of the tool 20 in between the mould parts 21a and 21b along the dividing line between the upper portion 20a and the lower portion 20b when these two portions are pushed together.

In connection with the cores 26 a closure 37 is furthermore provided, the outer shape of which corresponds to the outer shape of the casting box 32. The closure 37 can close the cavities which are constituted by the first mould parts 21a, the other mould parts 21b, and the cores 26, as the closure 37 for each cavity has a recess with a shape corresponding to the receiving end 3 of the tube and to the above imaginary cross-section which touches the nearest end of the projecting wall 16 and the flange 17. In the lower portion 20b of the tool are also provided ejection pieces 38 mounted to eject a moulded tube 1 from the tool when the cores 26 have been withdrawn and the upper portion 21a and the lower portion 21b are separated. The ejection pieces have an inactive position in which their surfaces just flush with the inner wall of the mould 21b.

The above tool 20 operates as follows:

As shown in FIG. 8a the upper portion 20a and the lower portion 20b are initially arranged to abut against each other. The positive mould 27 in the primary portion 20a1 in the upper portion 20a of the tool is in its withdrawn position and the negative mould 28 in the lower portion 20b is arranged to abut against the inner wall 24 of the mould part 21a. The distance of the surface 36 of the ejector 29 will be that of the distance from the surface 30 of the negative mould 28 previously mentioned. In this situation material for moulding the body 6 is fed from the chamber 33 and the material is allowed to harden.

When the body 6 is hardened the tool is opened as shown in FIG. 8b, as the upper portion 20a is withdrawn from its abutment against the lower portion 20b whereby the ejector 29 by means of its spring is thrust through the negative mould 28 so that the engagement of the body 6 with the recesses 16a, 17a in the negative mould 28 is resolved whereupon the body 6 is solely secured in the upper portion 20a by its engagement with the section between the projecting wall 16 and the surface which is later on to correspond to the surface of the intermediate portion 4 on a tube 1.

The upper portion 20a and the lower portion 20b are then turned relatively 180° and are brought together to abut against each other again, see FIG. 8a, the closure 37 is inserted towards the upper portion 20a and the cores 26 are pushed in from the side. The ejection pieces 38 are in their inactive position. The positive mould 27 is thrust into its projected position and thus pushes the moulded body 6 firmly against the cores 26. It will be understood that the mentioned end 35 of the positive mould 27 now flushes with the inner surface of the mould part 21a.

Now plastic material is fed into the cavities which are demarcated by the mould parts 21a and 21b, the cores 26, and the closure 37 as well as the bodies 6 whereupon the bodies 6 after hardening of the plastic material will be moulded form-closely in the tubes 1. Upon withdrawal of the portions 20a, 20b from each other and withdrawal of the cores 26, see FIG. 8b once more, the ejection pieces 38 will be made to operate whereby the finished tubes 1 are ejected.

Simultaneously with the moulding of the tubes 1 another number of bodies 6 have been moulded in the opposite side of the tool 20, which bodies 6, after another turning of 180° of the upper portion 20a in relation to the lower portion 20b, can be moulded in another number of tubes 1 etc.

I claim:

1. A plastic tube having an insertion end, an intermediate portion, and a receiving end, the tube adapted to connect a hose to a spigot, the tube having a hollow opening in an intermediate portion thereof, an elastic deformable body disposed in the hollow opening, the body adapted to be pierced by a hypodermic needle point, a sealing element disposed about the circumference of the body, the sealing element comprising a first wall projecting from the circumference of the body, parallel with a central axis of the tube, a flange projecting from an edge of the first wall, the flange projecting a short distance in a direction perpendicular to the tube axis, the tube having corresponding recesses for form-close reception of the first wall and flange therein.

2. The tube according to claim 1 wherein the sealing element further comprise a further projecting wall projecting from the circumference of the body parallel to the first wall.

3. A method for producing a plastic tube having an insertion end, an intermediate portion, and a receiving end, the tube having a bore therethrough and adapted to connect a hose to a spigot, the tube having a hollow opening in the intermediate portion thereof, an elastic deformable body arranged in the hollow opening, the body adapted to be pierced by a hypodermic needle point, the method comprising providing a first mold part and a second mold part, which define a cavity corresponding to the shape of the plastic tube, providing the elastic deformable body in the first mold part, placing a removable core defining the bore within the mold cavity, displacing the body into abutment with the core, and, filling the cavity with plastic so as to surround the core and body with plastic and solidifying the plastic to lock the body within the plastic tube in form-close engagement.

4. The method of claim 3 further comprising securing the body within the first mold part.

5. A tool for use in producing plastic tubes each of which has an insertion end, an intermediate portion and a receiving end, the intermediate portion having an elastic deformable body, arranged in a hollow opening therein, the body around its circumference having sealing elements concurring with the tube, the tool comprising an upper portion and a lower portion, the upper portion having an even number of first mold parts configured for molding a first half of the tube, the lower portion having a number of mold parts corresponding to half of the number of the first mold parts, the tool having an axis which is common for the upper and lower portions, the upper portion having a primary portion and a secondary portion, which extend on each side of the axis, means for molding bodies provided in each of the mold parts, removable cores locatable between the mold parts, cavities formed about the core corresponding to the shape of the tube, the upper portion being rotatable about the axis such that the first mold parts in the primary portion and the secondary portion respectively in turn are alignable with the second mold parts in the lower portion, means for displacing the molded bodies into the cavities, into partial abutment against the cores and partly against an inner wall of a section of the second mold parts which form the intermediate portion of the tube and means for supplying plastic to the cavities to form the tubes.

6. Tool according to claim 5, characterized in that the first mould parts (21a) comprise cavities corresponding to the first half part (1a) of at tube (1) from the insertion end (2) of the tube (1) to a cross-section placed in the tube, which cross-section touches the part of a flange (17) of the body (6) that is nearest to the receiving end (3) of the tube (1), a displacably mounted positive mould (27) and a negative mould (28) enclosing a displacably mounted ejector (29), which negative mould (28) has a surface (30) configured to abut against the inner wall (24) of the section (25) of the mentioned cavity which corresponds to the intermediate portion (4) of the tube (1) where the surface (30) has a recess (16a, 17a) corresponding to the projecting wall (16) and the flange (17) of the body (6), and that the positive mould (27) and the negative mould (28) have a cross-section corresponding to that of the body (6) and extend in each other's longitudinal direction, which negative moulds (28) with their ejectors (29) are arranged in the lower portion (20a) of the tool (20) to the side of the axis (A—A) which is opposite the second mould parts (21b).

7. Tool according to claims 6, characterized in that the second mould parts (21b) in the lower portion (20b) of the tool have a closure (37) with cavities corresponding to the first half part (1a) of a tube (1) from the receiving end (3) of the tube (1) to the cross-section placed in the tube (1), which cross-section touches the flange (17) of the body (6), that the other mould parts (21b) each comprises a core (26) adapted to be axially inserted into the cavity formed by the two cavities and the closures (37), and that the positive moulds (27) in the upper portion (20a) in the protruding position of the cores (26) in the cavities are in their protruding position in such a manner that the bodies (6) are made to rest against the cores (26).

8. Tool according to claims 6, characterized in that the positive mould (27) can be displaced in the first mould part (21a) between a withdrawn and a protruding position, as the end (35) of the positive mould (27) in the protruding position flushes with the inner wall of the mentioned cavity, that the surface (30) of the negative mould (28) in the closed position of the tool (20) abuts against the inner wall (24) of the cavity, while at the same time the positive mould (27) is in its withdrawn position, and that the ejector (29) is displacable in the direction of the positive mould (27) with a length corresponding to the thickness of a body (6).

9. Tool according to claims 8, characterized in that the second mould parts (21b) in the lower portion (20b) of the tool have a closure (37) with cavities corresponding to the first half part (1a) of a tube (1) from the receiving end (3) of the tube (1) to the cross-section placed in the tube (1), which cross-section touches the flange (17) of the body (6), that the other mould parts (21b) each comprises a core (26) adapted to be axially inserted into the cavity formed by the two cavities and the closures (37), and that the positive moulds (27) in the upper portion (20a) in the protruding position of the cores (26) in the cavities are in their protruding position in such a manner that the bodies (6) are made to rest against the cores (26).

10. Tool according to claims 5, characterized in that the second mould parts (21b) in the lower portion (20b) of the tool have a closure (37) with cavities corresponding to the first half part (1a) of a tube (1) from the receiving end (3) of the tube (1) to the cross-section placed in the tube (1), which cross-section touches the flange (17) of the body (6), that the second mould parts (21b) each comprises a core (26) adapted to be axially inserted into the cavity formed by the two cavities and the closures (37), and that the positive moulds (27) in the upper portion (20a) in the protruding position of the cores (26) in the cavities are in their protruding position in such a manner that the bodies (6) are made to rest against the cores (26).

* * * * *